(12) United States Patent
Matsumoto et al.

(10) Patent No.: US 7,700,042 B2
(45) Date of Patent: Apr. 20, 2010

(54) AUTOMATED ANALYZER

(75) Inventors: Tetsufumi Matsumoto, Fujisawa (JP);
Tetsuro Ikegaki, Shunan (JP); Hirotoshi Miyauchi, Yokohama (JP)

(73) Assignee: Tosoh Corporation, Shunan-shi (JP)

( * ) Notice: Subject to any disclaimer, the term of this patent is extended or adjusted under 35 U.S.C. 154(b) by 962 days.

(21) Appl. No.: 10/829,937

(22) Filed: Apr. 23, 2004

(65) Prior Publication Data

US 2004/0265173 A1 Dec. 30, 2004

(30) Foreign Application Priority Data

May 6, 2003 (JP) .............................. 2003-128447

(51) Int. Cl.
*G01N 35/02* (2006.01)
*G01N 35/04* (2006.01)
*G01N 35/10* (2006.01)

(52) U.S. Cl. ............................. 422/64; 422/63; 422/65; 436/43; 436/47; 436/50

(58) Field of Classification Search ............. 422/63–65, 422/100; 436/43, 50, 47
See application file for complete search history.

(56) References Cited

U.S. PATENT DOCUMENTS

| 3,900,289 | A | | 8/1975 | Liston | |
|---|---|---|---|---|---|
| 4,170,625 | A | | 10/1979 | Welch | |
| 4,863,693 | A | * | 9/1989 | Howell | 422/64 |
| 4,906,433 | A | * | 3/1990 | Minekane | 422/64 |
| 5,178,833 | A | * | 1/1993 | Covain | 422/64 |
| 5,358,691 | A | | 10/1994 | Clark et al. | |
| 5,599,501 | A | * | 2/1997 | Carey et al. | 422/64 |
| 5,795,784 | A | * | 8/1998 | Arnquist et al. | 436/50 |
| 2002/0134923 | A1 | * | 9/2002 | Watari et al. | 250/221 |

FOREIGN PATENT DOCUMENTS

| EP | 0 293 624 A2 | 12/1988 |
|---|---|---|
| EP | 0 410 688 A2 | 1/1991 |
| EP | 0 411 620 A2 | 2/1991 |
| EP | 1 243 892 A2 | 9/2002 |
| JP | 62-36182 | 2/1987 |
| JP | 9-145719 | 6/1997 |
| JP | 10-38892 | 2/1998 |
| JP | 2000-105247 | 4/2000 |
| JP | 2001-27643 | 1/2001 |
| JP | 2001-165936 | 6/2001 |
| WO | WO 92/05448 | 4/1992 |
| WO | WO 02/44740 A2 | 6/2002 |

* cited by examiner

*Primary Examiner*—P. Kathryn Wright
(74) *Attorney, Agent, or Firm*—Oblon, Spivak, McClelland, Maier & Neustadt, L.L.P.

(57) ABSTRACT

An automated analyzer for analyzing a specific component in a specimen includes a rotor, a specimen dispenser, a temperature controlling element, a stirrer, and a data analyzer. The rotor is provided with a plurality of specimen container holders for holding the specimen container containing the specimen, and a plurality of reaction container holders that correspond with each of the specimen container holders and hold the sealed reaction containers containing the reagent for reacting with the specimen. The specimen dispenser removes the specimen from the specimen container and dispenses the specimen into the reaction container. The temperature controlling element maintains the temperatures of the reaction container at a constant temperature. The stirrer uses magnetic force to stir a mixed solution of the reagent and the specimen in the reaction container. The data analyzer analyzes the mixed solution.

14 Claims, 9 Drawing Sheets

AUTOMATED ANALYZER

BACKGROUND OF THE INVENTION

1. Field of the Invention

The present invention relates to an apparatus for automatically analyzing trace components contained in biological samples (specimens) such as blood, serum, plasma or urine, and more particularly to an automated analyzer for analyzing the trace components in such specimens either biochemically or immunologically.

2. Description of the Related Art

In the field of clinical diagnosis, the use of analyzers for detecting specific components in a specimen collected from a subject and determining the concentration thereof, and then making a diagnosis of an illness or disease based on the results of this analysis has become widespread. These analyzers include multichannel biochemical analyzers which use enzyme reactions and other chemical reactions to analyze sugars, fats, proteins, and the like, and multichannel immunochemical analyzers that use specific interactions between antigens and antibodies to analyze hormones, tumor markers, and the like.

In order to avoid contamination among the specimens or the reaction fluids, some of these analyzers conduct the biochemical reactions or immunoreactions in individual disposable reaction containers, and in analyzers which use reaction containers that have been pre-filled with the reagents required for analyzing the specified components in the specimen, the use of disposable reaction containers is normal practice.

One example of a known analytical method is enzyme immunoassay (EIA) in which operations are conducted using enzyme labeled antibodies (or antigens). One specific example is known as a sandwich method, in which an antibody (or an antigen), for a specific component to be analyzed, immobilized in a suitable solid phase is used to capture the specific component, an enzyme labeled antibody or antigen (conjugate) is brought in contact to form an immunoreaction complex, any conjugate is removed (by BF separation), and a substrate which utilizes the activity of the enzyme to generate a measurable signal (for example, a variation in light absorbance or a variation in fluorescent intensity) is added. The resulting signal is then measured, the quantity of the enzyme is determined from a prepared calibration curve delineating the relationship between the signal intensity and the enzyme quantity, and this measured enzyme quantity is used to determine the quantity of the specific component being analyzed (see Japanese Patent No. 2,881,826).

In this type of EIA, a variety of different reagents, namely antibodies or antigens, must be used depending on the specific component to be analyzed, and consequently reaction containers containing each of the various reagents and sealed with a sealing member (hereafter described as "reagent cups") are prepared in advance for each specific component, and the appropriate sealed reagent cups containing the correct reagent are selected and used for each measurement.

An automated analyzer for use with this type of measurement method comprises: a reading device; a sample dispenser; a seal breaker; a BF separator; a substrate dispenser; a detector; and a data analyzer (see Japanese Patent Laid-Open Publication No. 2001-165936). The reading device reads an identification marking made up of symbols, letters and the like, which is printed on the surface of the sealing member covering the reagent cup and indicates the item for analysis. The sample dispenser extracts a specimen of a sample such as blood from a specimen container such as a blood collection tube, and dispenses the specimen into a reagent cup. The seal breaker breaks the sealing member on the reagent cup to open the upper surface of the cup so that the sample can be dispensed into the reagent cup by the above sample dispenser. The BF separator separates and removes (by BF separation) enzyme labeled antibodies that exist in a liquid phase state in the sample-containing reaction fluid in the reagent cup into which the sample has been dispensed. The substrate dispenser adds a substrate for the labeled enzyme to the reagent cup following completion of the BF separation. The detector detects the level of fluorescence, light absorbance, light emission, or the like, which is used for measuring the labeled enzyme activity in the reagent cup after a predetermined length of time following dispensing of the substrate by the substrate dispenser. The data analyzer confirms the existence of, or determining the concentration of, a specific substance based on the signal intensity of the signal detected by the detector, which correlates with the existence of, or the concentration of, the specific substance.

In the case of heterogeneous sandwich EIA analysis using an enzyme for labeling, the reagent cup contains water insoluble magnetizable beads containing an immobilized antibody that undergoes a distinctive bonding with the specific substance, and an enzyme labeled antibody that undergoes a distinctive bonding with the specific substance, which are in a freeze-dried state.

In those cases where, as described above, magnetizable beads are placed in the reagent cups, by positioning a plurality of magnets, with the magnetic poles in an alternating arrangement, on a movable magnet plate that can move back and forth along the direction of movement of the reagent cups, and then moving this movable plate back and forth, the magnetizable beads in the reagent cups can be moved, enabling a stirring action to be initiated inside the reagent cups (see Japanese Patent Publication No. Hei 6-28594).

A conventional automated analyzer described above is also equipped with a transport device, which comprises a specimen container transport system that uses a chain conveyor or the like to move a plurality of the specimen containers in an endless manner, and a reagent cup transport system that uses a chain conveyor or the like to move a plurality of the reagent cups in an endless manner. The analyzer is configured so that when the specimen container transported by the specimen container transport system reaches a defined dispensing position, a predetermined quantity of the specimen is dispensed into a corresponding reagent cup that has been transported into position by the reagent cup transport system.

Because of the requirement to provide two separate transport systems, namely the specimen container transport system and the reagent cup transport system, the analyzer tends to be quite large.

Furthermore, by extending the length of the chain conveyors in the reagent cup transport system, the number of different reagent cups that can be provided for analyzing a single specimen can be increased, but such lengthening of the conveyor causes a corresponding increase in the heat capacity of the reagent cup transport system, which in turn increases the time required to adjust the temperature of the system to the predetermined operating temperature, thereby increasing the time between switching the analyzer on and beginning actual analysis.

Consequently, especially in those cases where rapid analysis is required, it is desirable that the analyzer is available for use as soon as possible after switching the apparatus on.

SUMMARY OF THE INVENTION

The present invention was deviced in view of the above factors, and it is an object of the present invention to provide an automated analyzer which can be installed in a restricted space, can be used in a short time of switching on, and provides superior operability.

A first aspect of the present invention provides an automated analyzer for analyzing a specific component in a specimen by sucking the specimen from a specimen container containing the specimen, and dispensing the specimen into a reaction container containing a reagent to initiate a reaction between the specimen and the reagent, comprising: a rotor which can rotate about a vertical central axis, and is provided with a plurality of specimen container holders which are evenly spaced around a large diameter circle centered on the central axis, for holding respectively, in a removable manner, the specimen container containing the specimen, and a plurality of reaction container holders that correspond with each of the specimen container holders, for holding respectively, in a removable manner, the reaction container sealed for containing the reagent for reacting with the specimen; a rotor driver for rotationally driving the rotor; a specimen dispenser for sucking the specimen in the specimen container held by any one of the specimen container holders and dispensing the specimen into the reaction container held by a predetermined reaction container holder predetermined from the reaction container holders; a temperature controlling element which is disposed along a movement route of the reaction container held by any one of the reaction container holders and maintain the temperatures of the reaction container at a constant temperature; and a stirrer which is disposed along the movement route of the reaction container held by any one of the reaction container holders and uses magnetic force to stir a mixed solution of the reagent and the specimen in the reaction container.

In a second aspect of the present invention, the automated analyzer also comprises a washing apparatus disposed around the periphery of the rotor, for washing the inside of the reaction container with a washing solution discharged from a nozzle device and sucking and removing the washing solution from the inside of the reaction container by use of the nozzle device at a position along a rotational direction of the rotor used during measurement where the reaction between the specimen and the reagent has finished.

In a third aspect of the present invention, the automated analyzer also comprises a substrate dispenser disposed around the periphery of the rotor at a more downstream position in the rotational direction of the rotor than the washing apparatus, for dispensing a substrate into the reaction container washed by the washing apparatus.

In a fourth aspect of the present invention, the rotor comprises a rotor main body formed as a cylindrical member, and the reaction container holders are provided at a predetermined spacing around the periphery of an upper flange formed on the inner peripheral of the top edge of the rotor main body, and the specimen container holders are provided around the outer periphery of the rotor main body, directly opposing the reaction container holders.

In a fifth aspect of the present invention, when the specimen container is taller, the top edge of the specimen container held in any one of the specimen container holders and the top edge of the reaction container held in any one of the reaction container holders are at substantially the same height.

In a sixth aspect of the present invention, the rotor driver is driven intermittently, with a single step equivalent to a rotational angle corresponding with a pitch with which the specimen container holders are provided on the rotor.

In a seventh aspect of the present invention, the specimen dispenser comprises a revolving device for revolving a specimen dispensing nozzle about the central axis of the rotor, a radial movement device for moving the specimen dispensing nozzle along a radial direction of the rotor, and a lift device for raising and lowering the specimen dispensing nozzle.

In an eight aspect of the present invention, the temperature controlling element is formed in a shape of a circular plate, and contacts lower surfaces of the reaction container holders provided on the rotor.

In a ninth aspect of the present invention, the reaction container holders hold respectively the reaction container so that the bottom of the reaction container is able to be inserted through and project slightly from the bottom of corresponding one of the reaction container holders.

In a tenth aspect of the present invention, the automated analyzer also comprises a rotor home position detector for detecting a predetermined stop position of the rotor as a home position of the rotor.

In an eleventh aspect of the present invention, the automated analyzer also comprises a rotor home position detector for detecting a predetermined stop position of the rotor as a home position of the rotor, wherein the rotor comprises a washing port into which the nozzle device of the washing apparatus is inserted, which is provided between the nozzle device of the washing apparatus and a substrate nozzle of the substrate dispenser when the rotor is positioned at the stop position as the home position of the rotor.

In a twelfth aspect of the present invention, at the home position of the rotor, the rotor is driven by the rotor driver so that the washing port moves to, and stops beneath the nozzle device of the washing apparatus and beneath the substrate nozzle, and the washing port is used for washing the nozzle device of the washing apparatus, and for discharging the substrate from the substrate nozzle to eject any air bubbles trapped in the substrate.

In a thirteenth aspect of the present invention, the automated analyzer also comprises a specimen container height detector for detecting the height of the specimen container held in any one of the specimen container holders provided on the rotor.

In a fourteenth aspect of the present invention, the automated analyzer also comprises a specimen container height detector for detecting the height of the specimen container held in any one of the specimen container holders provided on the rotor, wherein a distance below a liquid surface inside the specimen container to which the specimen dispensing nozzle is lowered is determined in accordance with the height of the specimen container detected by the specimen container height detector.

DETAILED DESCRIPTION OF THE PREFERRED EMBODIMENTS

The present invention will be described in detail in accordance with embodiments shown in the accompanying drawings.

FIG. 1 through FIG. 6 show an embodiment of the automated analyzer of the present invention applied to an immunoassay apparatus that uses EIA procedures to analyze antibodies or antigens in a sample.

Figure 1:
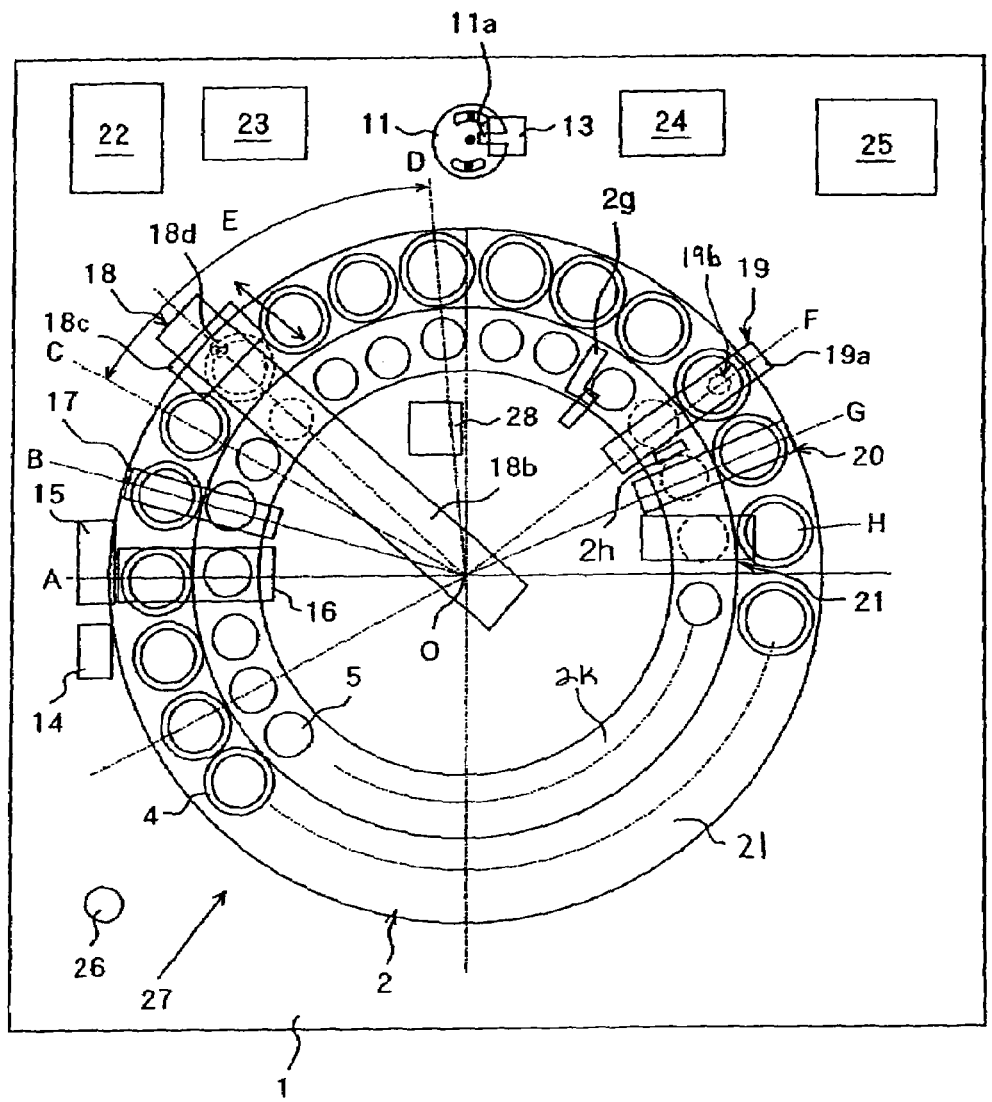
FIG. 1 is a top view showing an immunoassay apparatus according to an embodiment of the present invention.
Figure 2:
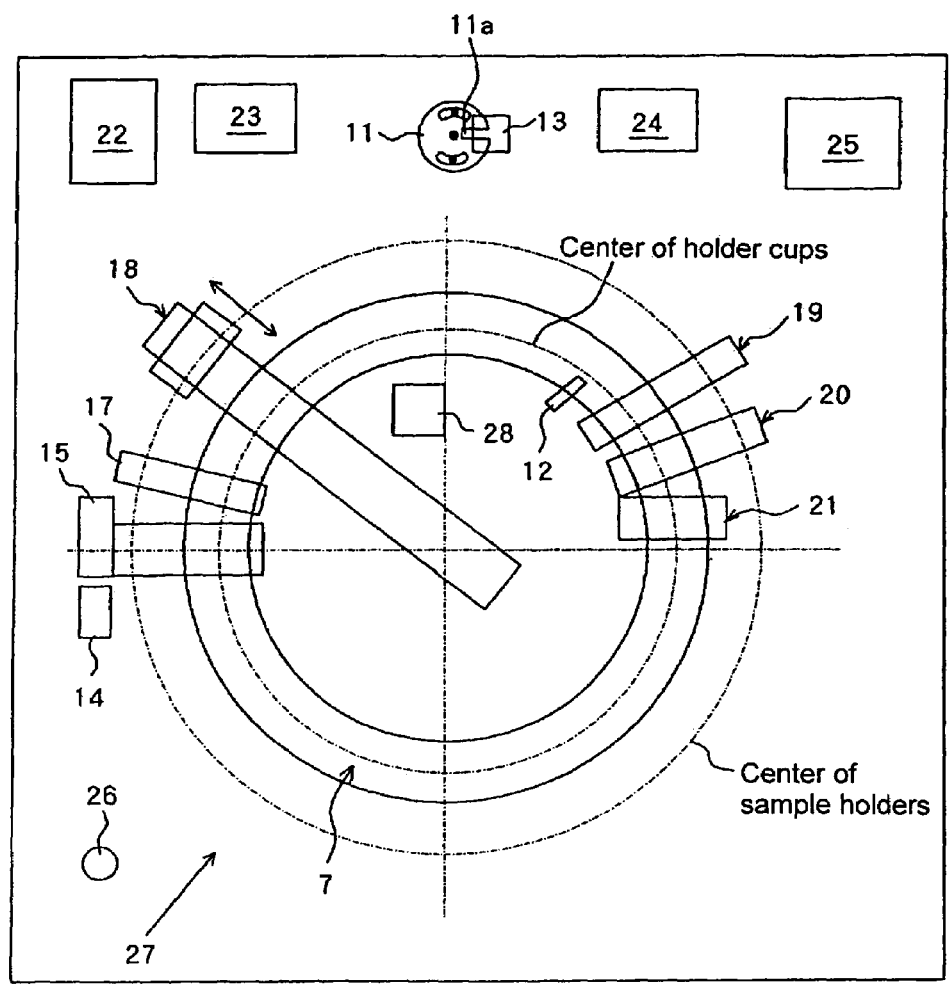
FIG. 2 is a top view of the immunoassay apparatus of FIG. 1 with the carousel removed.
Figure 3:
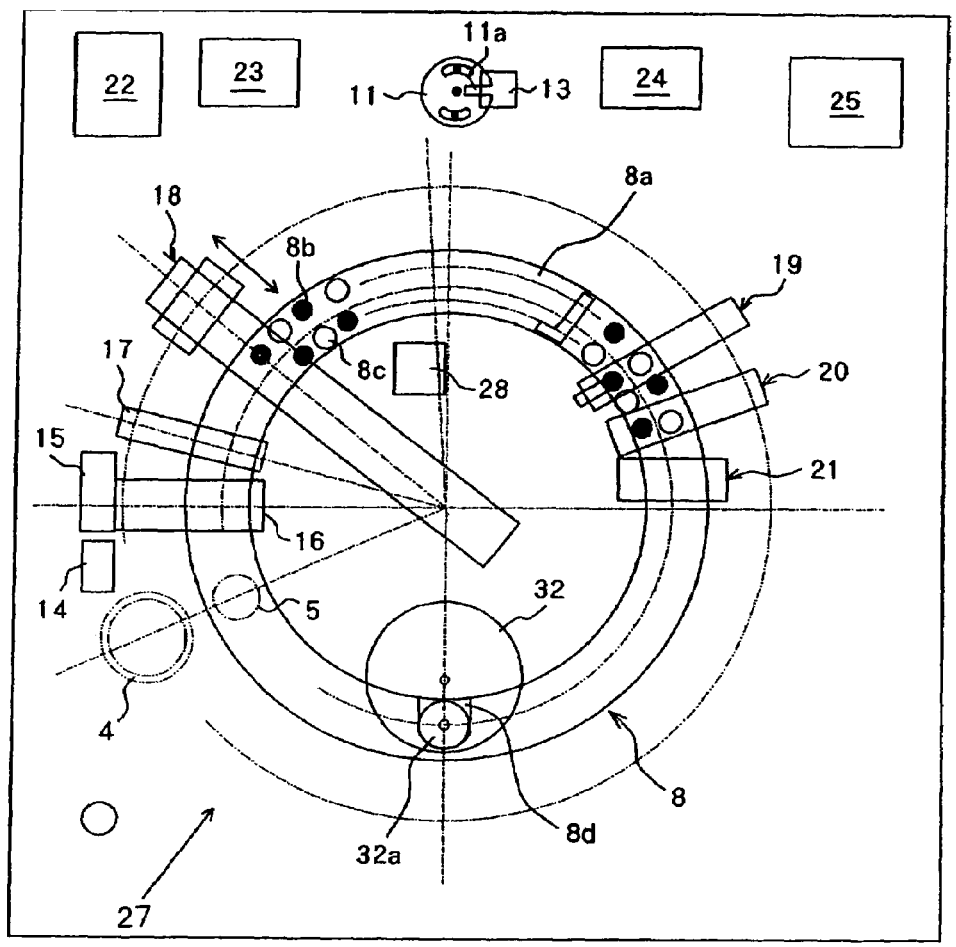
FIG. 3 is a top view of the immunoassay apparatus of FIG. 2 with the heater removed.
Figure 4:
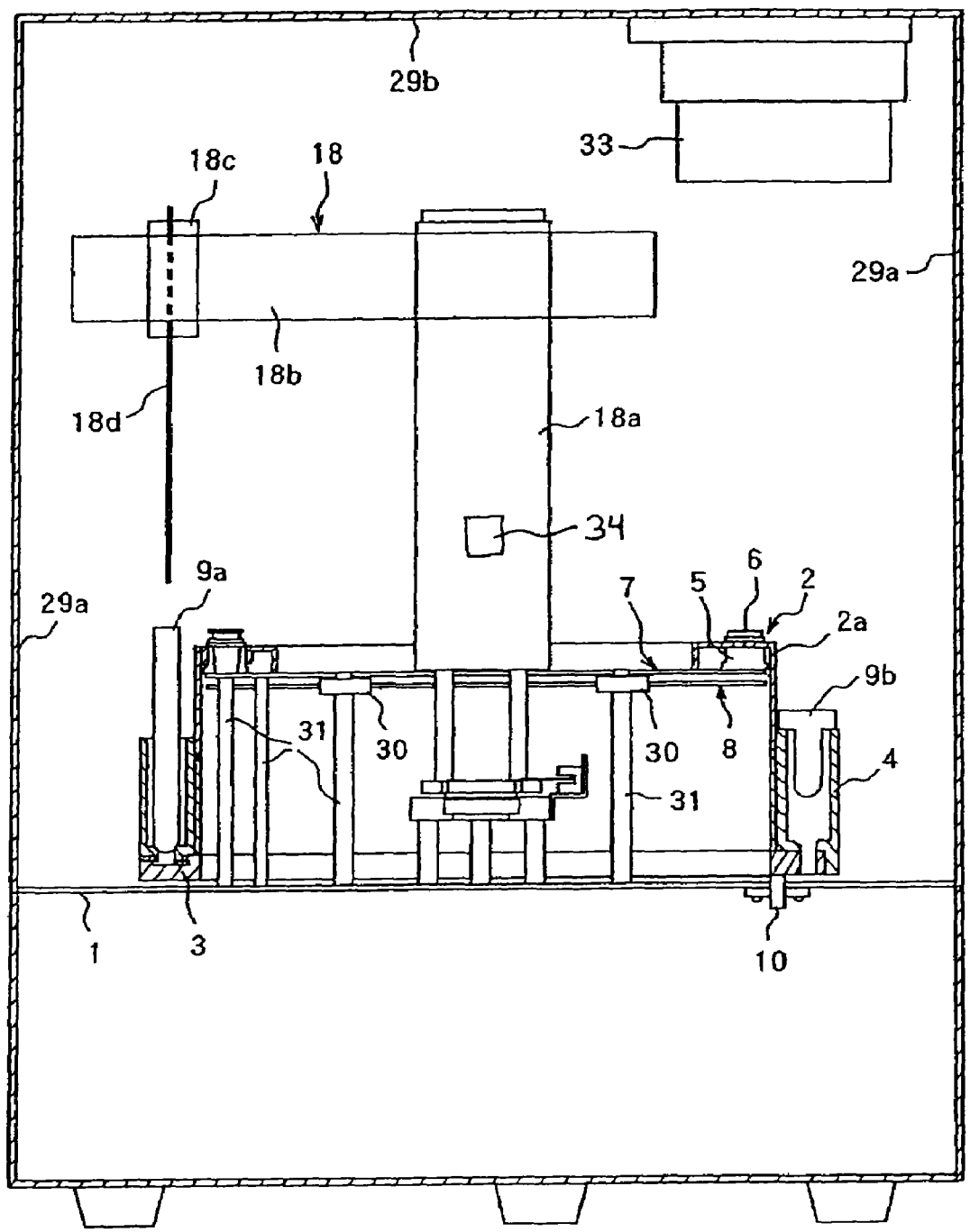
FIG. 4 is a central longitudinal sectional view along the position A of FIG. 1.
Figure 5:
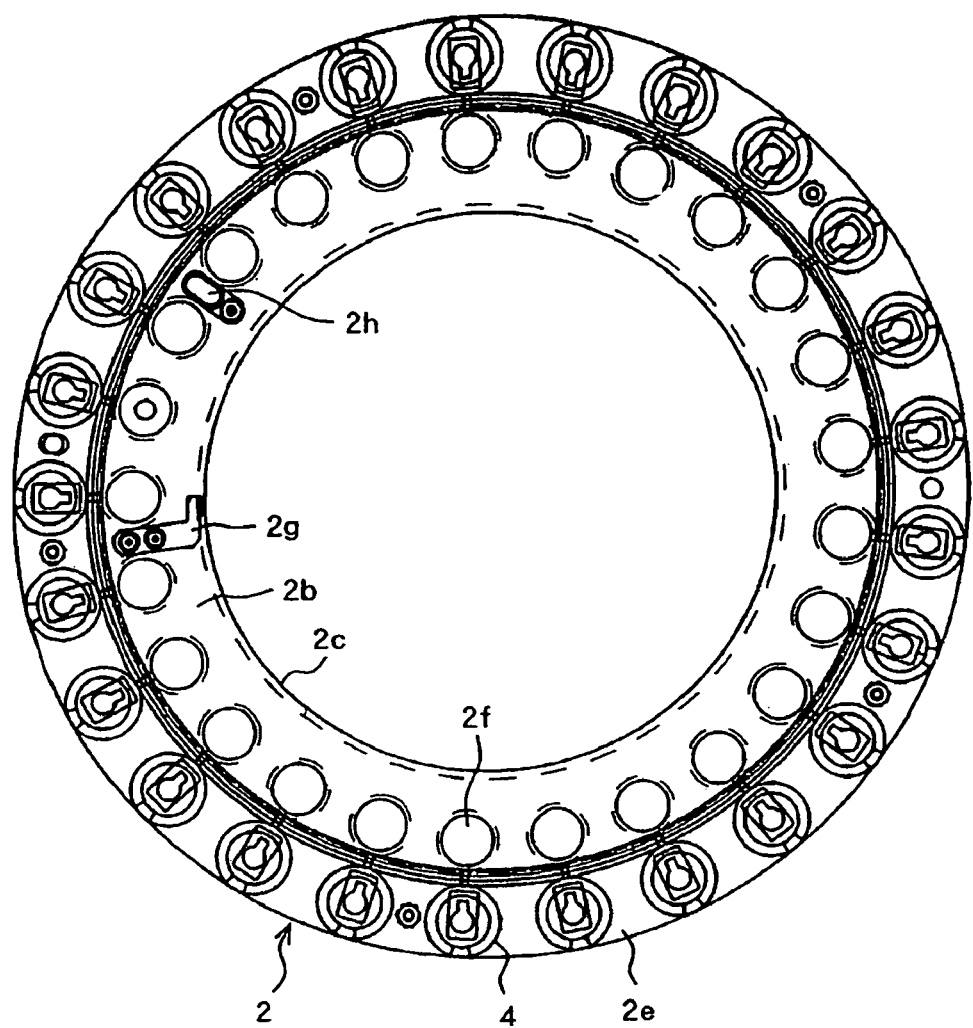
FIG. 5 is a top view of the carousel of FIG. 1.
Figure 6:
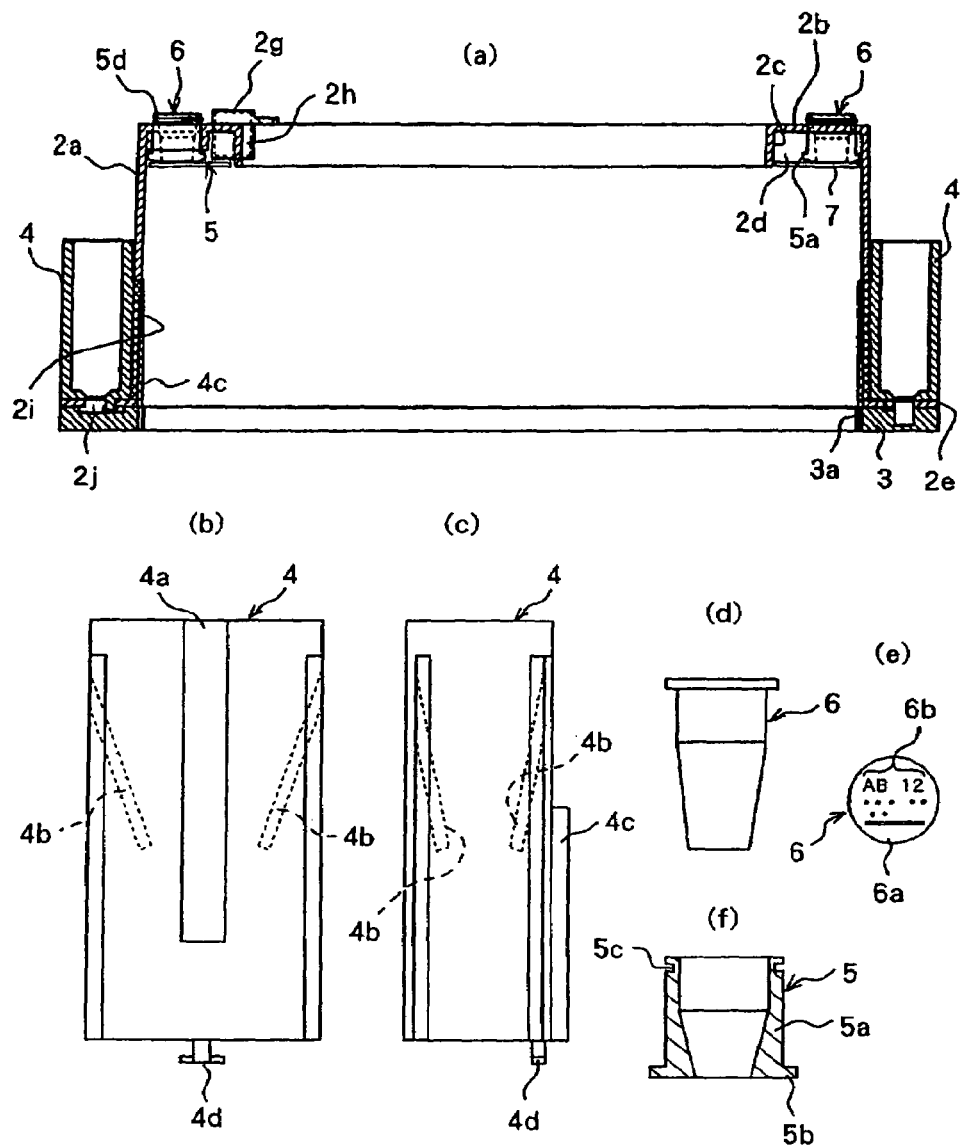
FIG. 6 shows a central longitudinal sectional view of the carousel of FIG. 5, as well as views of a specimen container holder, a reagent cup, and a cup holder.

FIG. 1 is a top view showing a schematic illustration of the immunoassay apparatus, FIG. 2 is a view of the apparatus of FIG. 1 with the carousel that represents the rotor removed, FIG. 3 is a view of the apparatus of the FIG. 2 with the circular plate shaped heater that represents the temperature controlling element removed, FIG. 4 is a longitudinal sectional view of FIG. 1, FIG. 5 is a plan view of the carousel of FIG. 1, and FIG. 6 shows the carousel of FIG. 5, wherein (a) shows a longitudinal sectional view of the carousel, (b) shows a front view of a specimen container holder for holding a tube-like specimen container, (c) shows a side view of the specimen container holder, (d) shows a side view of a reagent cup that represents a reagent-carrying reaction container, (e) shows a top view of the reagent cup, and (f) shows a side sectional view of a cup holder that represents a reaction container holder.

In the drawings, the reference numeral 1 represents a base plate of the immunoassay apparatus, and a cylindrical carousel 2 that functions as a rotor is attached to substantially the center of the base plate 1 so as to freely rotate. As shown in FIG. 2 and FIG. 4, a circular plate shaped heater 7 is attached to the apparatus base plate 1 substantially concentrically with the carousel 2 and in a position that corresponds with the position of reagent cups 6. In addition, as shown in FIG. 3 and FIG. 4, a circular plate shaped movable magnet plate 8 that functions as stirrer is attached to the apparatus base plate 1 below the heater 7, in a concentric arrangement with the carousel 2, and is able to move back and forth across the base plate 1.

As shown in FIG. 5 and FIG. 6, the carousel 2 comprises a cylindrical carousel main body 2a formed from a resin material such as polyacetal, together with a circular plate shaped upper flange 2b formed as a unit at the top inner peripheral section of the main body 2a, and an inner peripheral edge 2c of this upper flange 2b is bent downward, forming a downward facing concave section 2d surrounded by this inner peripheral edge 2c, the upper flange 2b, and the inner peripheral surface of the carousel main body 2a. Furthermore, an lower flange 2e is formed as a unit at the outer periphery 21 of the bottom of the carousel main body 2a. A circular plate shaped drive ring 3 is secured to the bottom surface of this lower flange 2e, and a drive gear that is not shown in the drawings meshes with a gear section 3a formed on the inner peripheral edge of the drive ring 3, and is rotated by a carousel drive motor that is not shown in the drawings (but which corresponds with the step motor PM6 shown in FIG. 7).

A plurality of specimen container holders 4 are mounted at equal intervals in the circumferential direction around the outer periphery 21 of the carousel main body 2a, and specimen containers can be either mounted in, or retrieved from, these holders along the vertical direction. Furthermore, a plurality of cup holder mounting apertures 2f, equal to the number of specimen container holders 4, are formed in the upper flange 2b of the carousel main body 2a, directly opposing the specimen container holders 4.

Cup holders 5 are inserted into these cup holder mounting apertures 2f, with a slight gap left between each holder and aperture.

Each cup holder 5 is formed as a single integrated unit from a member with superior thermal conductivity such as aluminum, and as shown in FIG. 6(f), comprises a holder main body section 5a formed in a cylindrical shape, and a flange section 5b that extends radially outwards from the bottom of the holder main body section 5a. Each cup holder 5 is inserted into a cup holder mounting aperture 2f from underneath, and is prevented from falling by attaching a C-ring 5d to a peripheral slot 5c formed in the upper section of the cup holder 5 once the cup holder 5 has been passed through the aperture 2f. Furthermore, the inner periphery of the holder main body section 5a is shaped so as to substantially conform with the exterior form of the reagent cup 6 shown in FIGS. 6(d) and (e). When the reagent cup 6 is mounted inside the cup holder 5 under its own weight, the bottom end of the reagent cup 6 protrudes slightly below the bottom of the cup holder 5.

When the carousel 2 is mounted in a rotatable manner to a predetermined position on the apparatus base plate 1, the bottom ends of the cup holders 5 contact the upper surface of the circular plate shaped heater 7, meaning that the bottom ends of the reagent cups 6 are lifted up slightly by contacting the upper surface of the heater 7. In this state, because the reagent cups 6 are held in a slightly raised state with respect to the cup holders 5, reagent cups 6 that have already been measured can be retrieved easily from their respective cup holders 5.

The height of the carousel main body 2a of the carousel 2 is set so that when a tall blood collection tube 9a such as that shown in FIG. 4 is mounted in a specimen container holder 4 as a specimen (sample) container, the top edge of this tall blood collection tube 9a and the top edge of the reagent cup 6 are at substantially the same height.

By so doing, in a configuration where the specimen containers are disposed at the outer periphery 21 of the carousel 2 and the reagent cups 6 are disposed at the inner periphery 2k, the tall blood collection tube 9a does not impede access when mounting an unused reagent cup 6 in a cup holder 5, or when retrieving a reagent cup 6 that has already undergone measurement from its cup holder 5. Furthermore, as shown in FIG. 4, when a short sample cup 9b is mounted into a specimen container holder 4 as a specimen container, the top edge section of the sample cup 9b is designed so as to protrude from the top edge of the specimen container holder 4.

Furthermore, the specimen container holders 4 are formed from the same material as the carousel main body 2a, and each comprises a cutout section 4a in the front face that enables the reading of a barcode printed on a sheet and attached to the surface of a specimen container mounted inside the holder, with the barcode functioning as a unique identification marker for that particular specimen, and specimen container supports 4b which are provided at four positions around the inner periphery and protrude in towards the center of the specimen container holder 4 to support the mounted specimen container. Furthermore, a rear surface protrusion 4c formed on the rear surface of the specimen container holder 4 engages with a slit 2i formed in the carousel main body 2a, and a bottom protrusion 4d engages with a mounting aperture 2j formed in the lower flange 2e, thereby enabling the specimen container holder 4 to be mounted to the carousel main body 2a without the use of screws or the like.

Rollers 10 are mounted to the apparatus base plate 1 at four positions which coincide with the outer periphery 21 of the carousel main body 2a, and the carousel 2 is supported by bringing the lower surface of the drive ring 3 into contact with these four rollers 10. Furthermore, pressure rollers which are not shown in the drawings are also provided at three equally spaced positions around the outer periphery of the drive ring 3, and by contacting the outer peripheral surface of the drive ring 3, these three pressure rollers support the carousel 2 so that the carousel 2 enables rotation about the central rotational axis.

Furthermore, a protrusion 2g that enables detection of the home position (hereafter abbreviated as HP) of the carousel 2 is provided on the upper surface of the carousel 2, and a washing tank 2h for the BF probe is provided between two cup holders 5.

In the drawings, the reference numeral 11 represents an encoder plate, which comprises a cutout section 11a and coupled directly to the motor shaft of a carousel drive motor (not shown in the drawings) that is a pulse motor. One revolution of this encoder plate 11 causes the carousel 2 to move one pitch position. A detector 12 (represented by a sensor S1 in FIG. 7) for detecting the home position of the carousel 2 is provided above the rotational route followed by the carousel 2, and when this carousel home position detector 12 detects the protrusion 2g on the carousel 2, the current position is deemed the HP for the carousel 2. At this point, if the cutout section 11a of the encoder plate 11 is simultaneously detected by another detector 13 (represented by a sensor S4 in FIG. 7) comprising a photosensor, then the control device determines that the pulse motor (the carousel drive motor) and the carousel 2 are connected correctly, whereas if a delay develops between the timing of detection by the detector 12 and that by the detector 13, then the rotational position of the encoder plate 11 is adjusted until the detection timings of the detector 12 and the detector 13 coincide with each other.

In FIG. 1 through FIG. 3, the region 27 indicated by an arrow at the bottom left of the figures is the region for mounting or retrieving specimen containers and reagent cups 6, and is fitted with an openable door that is not shown in the drawings. Furthermore, other than this door, the remaining side surfaces are enclosed by side wall members 29a as shown in FIG. 4, and the upper surface of the apparatus is also covered with a top plate 29b, meaning the interior of the immunoassay apparatus is isolated from the outside.

With the above mounting and retrieval region 27 functioning as the base point, the carousel 2 rotates intermittently in a clockwise direction. As the carousel 2 rotates, the height of each specimen container mounted in a specimen container holder 4 is detected from the side of the mounting and retrieval region 27 by a height detector 14 (represented by sensors S2 and S3 in FIG. 7) and a determination is made as to whether the specimen container is a tall blood collection tube 9a or a short sample cup 9b. The reason for checking the heights of the specimen containers at this point is to enable determination of the lowering distance for the dispensing nozzle which is described below. In the case where no specimen container is mounted in a specimen container holder 4, a judgment of "no specimen container" is made.

This height detector 14 comprises a pair of upper and lower sensor members that are able to slide up and over the specimen containers mounted in the specimen container holders 4 as the carousel 2 rotates, and a pair of upper and lower switch members which are switched on by each of the sensor members as they contact a detector tube while moving up into a withdrawn position.

When a tall blood collection tube 9a reaches this height detection position, both the upper and lower sensor members are activated and both the upper and lower switch members output an ON signal. In contrast, when a short sample cup 9b reaches the height detection position, only the lower sensor member is activated and only the lower switch member outputs an ON signal.

Reagent cups 6 are also mounted in their respective cup holders 5 at the mounting and retrieval region 27. The specimen container holders 4 and the cup holders 5 correspond, so that for each specimen container mounted in a specimen container holder 4, a corresponding reagent cup 6 is mounted in the cup holder 5 that corresponds with the specimen container holder 4 holding that specimen container. In those cases where a plurality of different items are to be measured for a sample from a single specimen container, the single specimen container is mounted in a single specimen container holder 4, and the reagent cups 6 for each of the items to be measured are mounted sequentially in cup holders 5, beginning with the cup holder 5 corresponding with the specimen container and then moving upstream relative to the direction of carousel rotation. In such cases, the present embodiment enables measurement of up to 5 items.

A barcode reader 15, which functions as identification information reading means for reading the unique identification information displayed on the surface of each specimen container, is disposed adjacent to the height detector 14 in a downstream position relative to the direction of the carousel 2 rotation, and is positioned at a height that corresponds with the cutout sections 4a provided in the specimen container holders 4. This barcode reader 15 reads the barcode as the unique identification information for each specimen container that is displayed on the surface of the specimen container through this cutout section 4a. The unique identification information for the specimen container read by the barcode reader 15 is transmitted to the control device, which controls the overall operation of the immunoassay apparatus.

Furthermore, the specimen container barcode reading position A for the barcode reader 15 is a stop position for the carousel 2, and at this position the specimen container holder 4 and the cup holder 5 are aligned in the radial direction.

In addition, in this embodiment, 25 specimen container holders 4 and 25 cup holders 5 are provided at equal intervals around the circumference of the carousel 2, and consequently if the carousel 2 is rotated in 14.4 degree steps (hereafter referred to as a 1-step rotation), then each specimen container holder 4 and corresponding cup holder 5 can be moved progressively.

An imaging device 16 such as a CMOS camera for reading an identification marking 6b, which is displayed on the surface of a sealing member 6a (see FIG. 6(e)) covering the top opening of the reagent cup 6 mounted in the cup holder 5 and indicates the item for analysis, is also disposed at the same position as the barcode reading position, but is positioned above the cup holder 5. The analysis item for the reagent cup 6 read by the imaging device 16 is stored for each specimen.

A seal breaker 17 is disposed at a position B, which is for example a 1-step rotation of the carousel 2 from the position A, and this seal breaker 17 uses a needle-like breaker (not shown in the drawings) that moves up and down to pierce the sealing member 6a covering the reagent cup 6 from above. The breaker is then pushed down further to spread and open the broken sealing member 6a, thereby exposing the top opening of the reagent cup 6, and is then raised in preparation for the next 1-step rotation of the carousel 2.

The region between a position C, which is a 1-step rotation from the position B, and a position D which is a further 4-step rotations from the position C is defined as the sample dispensing region E, and a sample dispenser 18 dispenses samples from the specimen containers held by the specimen container holders 4 within this sample dispensing region E into the corresponding reagent cups 6 that have been opened by the seal breaker 17.

In this embodiment, the sample dispenser 18 comprises a revolving tower 18*a*, a horizontally extended arm 18*b*, a nozzle support 18*c*, and a sample dispensing nozzle 18*d*. The revolving tower 18*a* (see FIG. 4) has its rotational center positioned at the rotational center position O of the carousel 2, and extends in a vertical direction, and is rotationally driven within the sample dispensing region E by a revolving drive mechanism that uses a revolving motor (not shown in the drawings, but equivalent to the motor PM3 in FIG. 7) formed from a pulse motor as the drive source. The horizontally extended arm 18*b* is supported so that it enables the arm to be raised and lowered with respect to the revolving tower 18*a*, and is raised and lowered by a lift drive mechanism that uses a lift motor 34 ( equivalent to the motor PM1 in FIG. 7) formed from a pulse motor as the drive source. The nozzle support 18*c* is supported so that it enables horizontal movement with respect to the arm 18*b* and is moved horizontally by a horizontal movement motor (not shown in the drawings, but equivalent to the motor PM2 in FIG. 7) formed from a pulse motor. The sample dispensing nozzle 18*d* is supported by the nozzle support 18*c* with the tip of the nozzle facing downwards.

The top end of the dispensing nozzle 18*d* is connected to a sample dispensing syringe 22 formed from a plunger-type precision pump by a flexible connection pipe that is not shown in the drawings, and this syringe sucks a predetermined quantity of the sample from inside a specimen container and dispenses the sample into a reagent cup 6.

In the sample dispenser 18, the position in which the arm 18*b* is stopped at the position C, and the nozzle support 18*c* is stopped in a position that locates the dispensing nozzle 18*d* directly above either the specimen container holder 4 or the cup holder 5 is deemed the home position for the dispensing nozzle 18*d*, and in the following description, the position above the cup holder 5 at position C is deemed the home position (hereafter abbreviated as HP).

When the carousel 2 undergoes a 1-step rotation, and a specimen container mounted in a specimen container holder 4 reaches the position C, the sample dispenser 18 drives the horizontal movement motor to move the nozzle support 18*c* out towards the tip of the arm 18*b*, and once the sample dispensing nozzle 18*d* is positioned directly above the specimen container the horizontal movement motor is stopped.

Subsequently, the lift motor 34 is activated, and the arm 18*b* is lowered until the dispensing nozzle 18*d* is inserted into the specimen container.

The dispensing nozzle 18*d* is formed from a conductive material such as stainless steel, and when the tip of the dispensing nozzle 18*d* reaches the liquid surface in the specimen container, the liquid surface is detected by a liquid surface detection circuit (not shown in the drawings). The lift motor 34 is then driven further to lower the dispensing nozzle 18*d* into the sample inside the specimen container. Because the height of the specimen container has been determined in advance by the height detector 14, the lift motor 34 is instructed to use a deep insertion in the case of a tall blood collection tube 9*a*, as the bottom of the specimen container sits at a low position enabling the dispensing nozzle 18*d* to be inserted deeply into the tube without causing any damage, whereas in the case of a short sample cup 9*b*, the lift motor 34 is instructed to use a shallow insertion, as the bottom of the specimen container sits at a higher position.

A predetermined quantity of sample is sucked by the sample dispensing syringe 22, the lift motor 34 is instructed to raise the arm 18*b*, and the dispensing nozzle 18*d* is removed from the specimen container and then moved by the horizontal movement motor to the dispensing nozzle HP. At the dispensing nozzle HP, the height from the tip of the dispensing nozzle 18*d* down to the reagent cup 6 is constant, and consequently from this point the lift motor 34 is activated and the arm 18*b* is lowered by a predetermined quantity so as to insert the tip of the dispensing nozzle 18*d* to a predetermined depth inside the reagent cup 6. The sample dispensing syringe 22 then discharges and the sucked sample is dispensed into the reagent cup 6. The lift motor 34 is then activated again, the arm 18*b* is raised, and the dispensing nozzle 18*d* is returned to the HP.

One cycle of this dispensing process is completed very quickly, and there is still time available before the next 1-step rotation of the carousel 2, and consequently during this available time the revolving motor is activated, rotating the revolving tower 18*a* in a clockwise direction, so that the arm 18*b* revolves through the horizontal plane in the clockwise direction. When the arm 18*b* reaches the position D, the horizontal movement motor is activated and the nozzle support 18*c* is moved horizontally towards the rotational center O. When the dispensing nozzle 18*d* reaches a position above an dispensing water tank 28 used for washing the dispensing nozzle 18*d*, the horizontal movement motor is stopped, the lift motor 34 is activated, and the arm 18*b* is lowered by a predetermined level, immersing the dispensing nozzle 18*d* in the washing solution inside the dispensing water tank 28.

Once the dispensing nozzle 18*d* is immersed in the washing solution inside the dispensing water tank 28, the suction and discharge operations of the dispensing syringe 22 are repeated a number of times, thoroughly washing the dispensing nozzle 18*d*, the dispensing syringe 22, and the inside of the connection pipe linking the two. Then, when the next 1-step rotation of the carousel 2 is approaching, the dispensing nozzle 18*d* is returned to the dispensing nozzle HP using the opposite operations to those described above, in preparation for the next dispensing process. At this time, a warning lamp 26 provided on the apparatus base plate 1 within the mounting and retrieval region 27 is lit or begins to flash, informing the operator that the next rotation of the carousel 2 is approaching, and prompting the mounting or retrieval of specimen containers and/or reagent cups 6.

Provided a specimen container is mounted in the specimen container holder 4 of the carousel 2, a dispensing operation is conducted into the corresponding reagent cup 6 sitting directly inside that specimen container. However, in the case where up to 5 different measurements are conducted on a specimen from a single specimen container (hereafter this type of multiple measurement is referred to as a "multi-dispensing"), although reagent cups 6 will be mounted in the second and subsequent cup holders 5, no specimen containers are mounted in the corresponding specimen container holders 4 sitting directly outside the second and subsequent cup holders 5. A multi-dispensing corresponds with a state where OFF signals from both the upper and lower switch members of the height detector 14, and/or an "unreadable" signal from the barcode reader 15 are input into the control device, but reading of the identification information by the imaging device 16 occurs normally. Accordingly, the control device instructs the sample dispenser 18 to dispense the sample inside the specimen container into the second and subsequent reagent cups 6 at the dispensing nozzle HP.

When a multi-dispensing commences, the second reagent cup 6 is located at the position C and the specimen container is positioned a 1-step rotation from the position C. When the third reagent cup 6 reaches the position C the specimen container has undergone a further 1-step rotation, and in the case where a maximum fifth reagent cup 6 has reached the position C, the specimen container has reached the position D.

As a result, the sample dispenser 18 is driven by the revolving motor in 1-step rotations from the position C to as far as the position D, and one cycle of the dispensing process described above is performed at each of the positions within the dispensing region D. For example, in the case in which three measurements are performed using a single sample, first a sample is sucked up by the dispensing nozzle 18d from the specimen container at a position 1-step rotation away from the position C, and the arm 18b is then returned to the position C, the dispensing nozzle 18d is returned to its HP, and the sample is dispensed into the second reagent cup 6. Then, when the third reagent cup 6 reaches the position C, a sample is sucked up by the dispensing nozzle 18d from the specimen container at a position 2-step rotations away from the position C, and the dispensing nozzle 18d is then returned to its HP as above, and the sample is dispensed into the third reagent cup 6.

On the next 1-step rotation of the carousel 2, the height detector 14 or the barcode reader 15 detect the fact that a specimen container is mounted in the specimen container holder 4 now located at the position C, and this detection can be used to determine the completion of the multi-dispensing. Of course, information detailing the multi-dispensing could also be manually input into the control device.

The circular plate shaped heater 7 is disposed beneath the carousel 2, and adjusted the temperature to a predetermined temperature (for example, 37 degrees Celsius) by the control of the control device. This heater 7 must maintain the temperature inside the reagent cups 6 at a constant value, allowing the reaction inside the reagent cups 6 to proceed, from the position C where the sample is dispensed into the reagent cup 6, through until a detection position H, where measurements are conducted following the dispensing of a substrate into the reagent cup 6 at a substrate dispensing position G. However in this embodiment, because of ease of manufacture, the heater 7 is formed with the heater element extending across the entire surface of the circular plate shaped hard base plate, and the heater 7 contacts the flange sections 5b at the bottom of all of the cup holders 5, leaving a slight gap between the inner peripheral surface of each cup holder 5 and the corresponding reagent cup 6. As a result, the cup holders 5 can be efficiently maintained at the predetermined temperature at all times, and even when an unused reagent cup 6 is mounted in a cup holder 5, there is little decrease in temperature, and the time required to reach the predetermined temperature following dispensing can also be reduced.

Furthermore, the bottom of the reagent cup 6 penetrates into the opening at the bottom of each cup holder 5, meaning each reagent cup 6 also contacts the heater 7 directly, which enables the temperature inside the reagent cups 6 to be maintained efficiently at the predetermined value.

In addition, because the concave section 2d is formed in a circumferential direction beneath the upper flange 2b of the carousel 2, and the heater 7 is positioned opposing this concave section 2d, warm air is trapped within the concave section 2d, further improving the heat retention properties, and enabling the temperature inside the reagent cups 6 to be maintained even more efficiently.

Furthermore, because the carousel 2 is configured with the reagent cups 6 positioned on the inside of the carousel main body 2a and the sample-carrying specimen containers positioned on the outside, and with the heater 7 disposed only on the inside of the carousel main body 2a, heat from the heater 7 is not transferred to the samples contained in the specimen containers, thereby isolating the samples in the specimen containers from any adverse heating effects.

On the other hand, the circular plate shaped movable magnet plate 8 is disposed beneath the heater 7 with a suitable spacing therebetween, and as shown in FIG. 3, a plurality of magnets 8b, 8c are disposed around the circumference of the movable magnet plate main body 8a, with the magnetic poles in an alternating arrangement (shown as black and white circles), from the position C where the samples are dispensed into the reagent cups 6 through until the detection position H. When the movable magnet plate main body 8a is moved back and forth, the magnetizable beads inside the reagent cups 6 also move, causing a stirring action inside the reagent cups 6.

As shown in FIG. 4, the movable magnet plate main body 8a of this movable magnet plate 8 is supported in a rotatable manner by engaging with the circumferential slots of a plurality of guide pulleys 30 formed along both the inner peripheral and outer peripheral edges of the movable magnet plate main body 8a, which is secured to the apparatus base plate 1. These guide pulleys 30 are provided on a plurality of support bars 31 which are secured to the apparatus base plate 1 and extend vertically upwards. Furthermore, a slot 8d that extends in a radial direction is formed in the inner peripheral surface of the movable magnet plate main body 8a, and a cam follower 32a provided on an eccentric cam plate 32, which is rotated using a reciprocating drive motor (not shown in the drawings, but equivalent to the motor PM4 in FIG. 7) formed from a pulse motor as the drive source, engages with this slot 8d, causing the movable magnet plate main body 8a to rotate back and forth as the eccentric cam plate 32 undergoes rotation in a single direction.

The circular plate shaped heater 7 is secured to the top of the support bars 31.

A washing device 19 is disposed at a position F, which is designated as the washing position, and by the time a reagent cup 6 reaches this position F, where the reaction that started at the position C has already progressed satisfactorily.

The washing device 19 is disposed at a stop position of the carousel 2, and comprises a BF probe (not shown in the drawings), for example, with a double nozzle structure (nozzle device 19b) positioned above the reagent cup 6 with the bottom up, and a BF probe lifting gear 19a that enables the BF probe to be raised and lowered.

When a 1-step rotation of the carousel 2 brings a reagent cup 6 mounted in a cup holder 5 of the carousel 2 to the position F, the BF probe is inserted inside the reagent cup 6, and the discharge action of a BF syringe 23 is used to inject washing water, which has been heated to a predetermined temperature by a washing water heater 24, through the BF probe into the reagent cup 6. Subsequently, the suction action of a waste water pump (not shown in the drawings) is used to suck, and discharge the liquid from inside the reagent cup 6. These discharge and suction operations are repeated, and on completion of this so-called BF separation which washes the inside of the reagent cup 6, the BF probe lifting gear 19a is raised using a BF probe motor (not shown in the drawings, but equivalent to the motor PM7 in FIG. 7) formed from a pulse motor as the drive source, via a BF probe lift drive mechanism, thereby removing the BF probe from the reagent cup 6 and completing the BF separation process.

Following completion of the BF separation process, the carousel 2 undergoes a further 1-step rotation, and the reagent cup 6 that has been subjected to the BF separation process reaches the position G.

A substrate dispenser 20 is disposed at the position G, and a downward facing substrate nozzle that points towards the reagent cup 6 is fitted to this substrate dispenser 20. The action of a substrate syringe 25 is used to dispense substrate from the substrate nozzle positioned above the reagent cup 6, and this addition of the substrate causes the generation of a measurable signal (which is detected as, for example, a variation in light absorbance, a variation in fluorescent intensity, or the emission of light) due to the enzyme activity.

The next 1-step rotation of the carousel 2 moves the reagent cup 6, containing the added substrate at the position G, to the position H.

A data analyzer 21 is disposed at the position H. In this embodiment, the data analyzer 21 uses a fluorescence detector, which measures the fluorescent intensity or the like inside the reagent cup 6, and then sends the result of the measurement to the control device. The control device outputs the measurement results to a printer 49, which prints them onto recording paper.

When the carousel 2 is positioned in its home position, the BF probe washing tank 2h provided on the upper surface of the carousel 2 is positioned between the BF probe at the position F and the substrate nozzle of the substrate dispenser 20. In other words, the ½-step (7.2 degrees) rotation of the carousel 2 in a counterclockwise direction from its HP moves and positions the BF probe washing tank 2h directly below the BF probe. In this position, the BF probe is lowered and immersed in the washing solution inside the BF probe washing tank 2h, and the discharge action of the BF syringe 23 and the suction action of the waste water pump are repeated, which sucks the washing solution from the BF probe washing tank 2h up through a BF probe suction pipe, and discharges this sucked washing solution out through a BF probe discharge pipe, thereby washing the BF probe.

Furthermore, the ½-step rotation of the carousel 2 in a clockwise direction from its HP moves and positions the BF probe washing tank 2h directly below the substrate nozzle. In this position, the suction and discharge actions of the substrate syringe 25 are repeated, thereby ejecting from the substrate nozzle any air bubbles trapped in the substrate.

The operations for rotating the carousel 2 ½-step in both the counterclockwise direction and the clockwise direction in order to wash the BF probe and eject air bubbles from the substrate nozzle respectively, can be performed either during startup of the immunoassay apparatus, or at a predetermined time interval.

Figure 7:
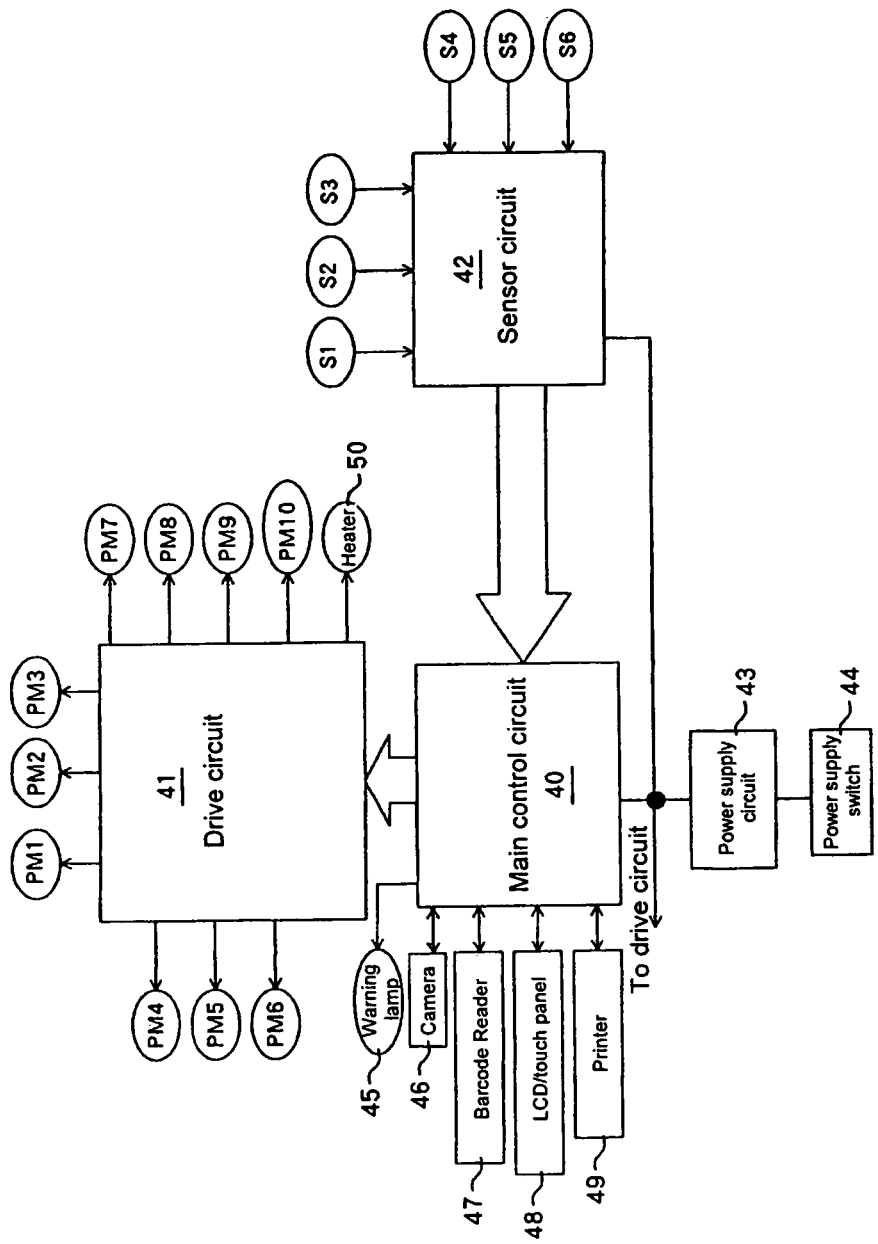
FIG. 7 is a block diagram showing a control device of the immunoassay apparatus of FIG. 1.

The control device for the immunoassay apparatus of the present embodiment is shown in FIG. 7.

In the control device of this embodiment, a main control circuit 40 outputs a variety of different drive signals to a drive circuit 41, which in turn controls the driving of a series of pulse motors PM1 to PM10 and a heater 50. Furthermore, control of the driving of each of the motors PM1 to PM10, and temperature control of the heater 50 is performed on the basis of sensor signals input into a sensor circuit 42 from sensors S1 to S5.

The motor PM1 is the lift motor 34 for raising and lowering the arm 18b in the sample dispenser 18, the motor PM2 is the horizontal movement motor for moving the nozzle support 18c of the sample dispenser 18 in a horizontal direction, and the motor PM3 is the revolving motor for rotating the revolving tower 18a of the sample dispenser 18.

The motor PM4 is the reciprocating drive motor for driving the movable magnet plate 8 back and forth, the motor PM5 is the seal breaker motor for moving the breaker of the seal breaker 17 up and down, the motor PM6 is the carousel drive motor for performing rotational driving of the carousel 2, and the motor PM7 is the BF probe motor for raising and lowering the BF probe.

The motor PM8 is the substrate syringe motor of the substrate dispenser 20, the motor PM9 is the washing syringe motor of the washing device 19, and the motor PM10 is the injection syringe motor of the sample dispenser 18. The reference numeral 50 represents the heater for maintaining the reagent cups 6 at a constant temperature.

The sensor S1 is the sensor for detecting the home position of the carousel 2, the sensor S2 is the sensor for detecting tall specimen containers, the sensor S3 is the sensor for detecting short specimen containers, the sensor S4 is the sensor for detecting one pitch of the drive motor PM6 of the carousel 2, the sensor S5 is the sensor for detecting the liquid surface level using the sample dispensing nozzle 18d, and the sensor S6 is the sensor for detecting the temperature of the heater 50.

The reference numeral 43 represents the power supply circuit for supplying power to the main control circuit 40, the drive circuit 41, and the sensor circuit 42, and the reference numeral 44 represents the power supply switch for the immunoassay apparatus.

The reference numeral 45 represents the warning lamp for warning of events such as the impending start of rotation of the carousel 2, the reference numeral 46 represents the camera for reading the identification information displayed on the sealing member of each reagent cup 6, the reference numeral 47 represents the barcode reader for reading the barcode displayed on each specimen container, the reference numeral 48 represents a display unit comprising a liquid crystal display device (LCD), a touch panel, and a keyboard or the like combined in a single unit and provided on the outside surface of the immunoassay apparatus, and the reference numeral 49 represents a printer for printing measurement results onto recording paper.

As follows is a description of the operation of the control device shown in FIG. 7, based on the flowcharts shown in FIG. 8 and FIG. 9.

Figure 8:
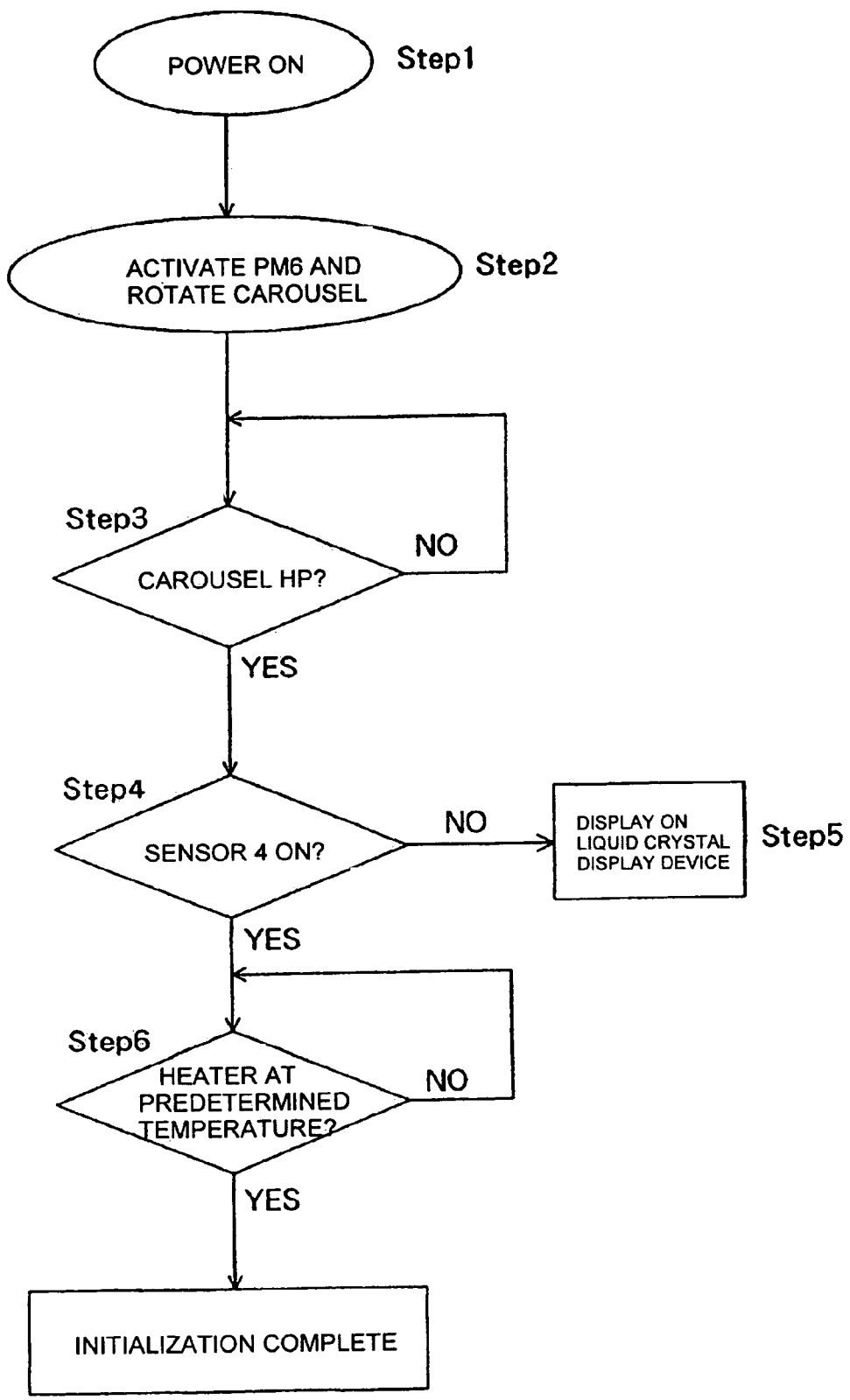
FIG. 8 is a flowchart showing an initialization process for the control device of FIG. 7.

FIG. 8 is a flowchart showing the initialization process conducted when the power supply switch is turned on.

In FIG. 8, when the power supply switch 44 is turned on (Step 1), the motor PM6 is activated and undergoes step rotation in the forward direction, causing the carousel 2 to rotate intermittently in the clockwise direction (Step 2). Power supply to the heater 50 is also started. At this point, the motor PM4 may be activated to start the back and forth movement of the movable magnet plate 8. Alternatively, the motor PM4 may be activated after completion of the initialization process.

When the sensor S1 detects that the carousel 2 has reached its HP (Step 3), a judgment is made as to whether or not the sensor S4 for detecting the rotational position of the encoder plate 11 of the carousel drive motor PM6 is ON (Step 4), and if the carousel 2 is stopped and the sensor S4 is OFF, then a fault is determined to have occurred in the driving of the carousel 2, and this fault is displayed on the liquid crystal display device (Step 5). The carousel drive motor is then stopped.

If the carousel 2 is stopped and the sensor S4 is ON, then the carousel 2 is judged to be functioning normally.

Next, when the detected temperature from the sensor S6 reaches the predetermined control temperature of the heater 50 (Step 6), this initialization process ends, and the apparatus moves to a standby mode, waiting for measurements.

Alternatively, when the carousel 2 is positioned at the HP and the sensor S4 at Step 4 is ON, the carousel 2 may first be rotated ½-step in the counterclockwise direction, and the motor PM7 is activated to insert the BF probe in the BF probe washing tank 2h. Then, the motor PM9 is activated to wash the BF probe through a series of suction and discharge operations through the BF probe, the BF probe is returned to its raised position, and a 1-step rotation of the carousel 2 in the clockwise direction is then conducted. Then, the motor PM9 is activated and a series of suction and discharge operations of the substrate syringe are used to discharge substrate from the substrate nozzle into the BF probe washing tank 2h while ejecting any air bubbles trapped in the substrate.

Figure 9:
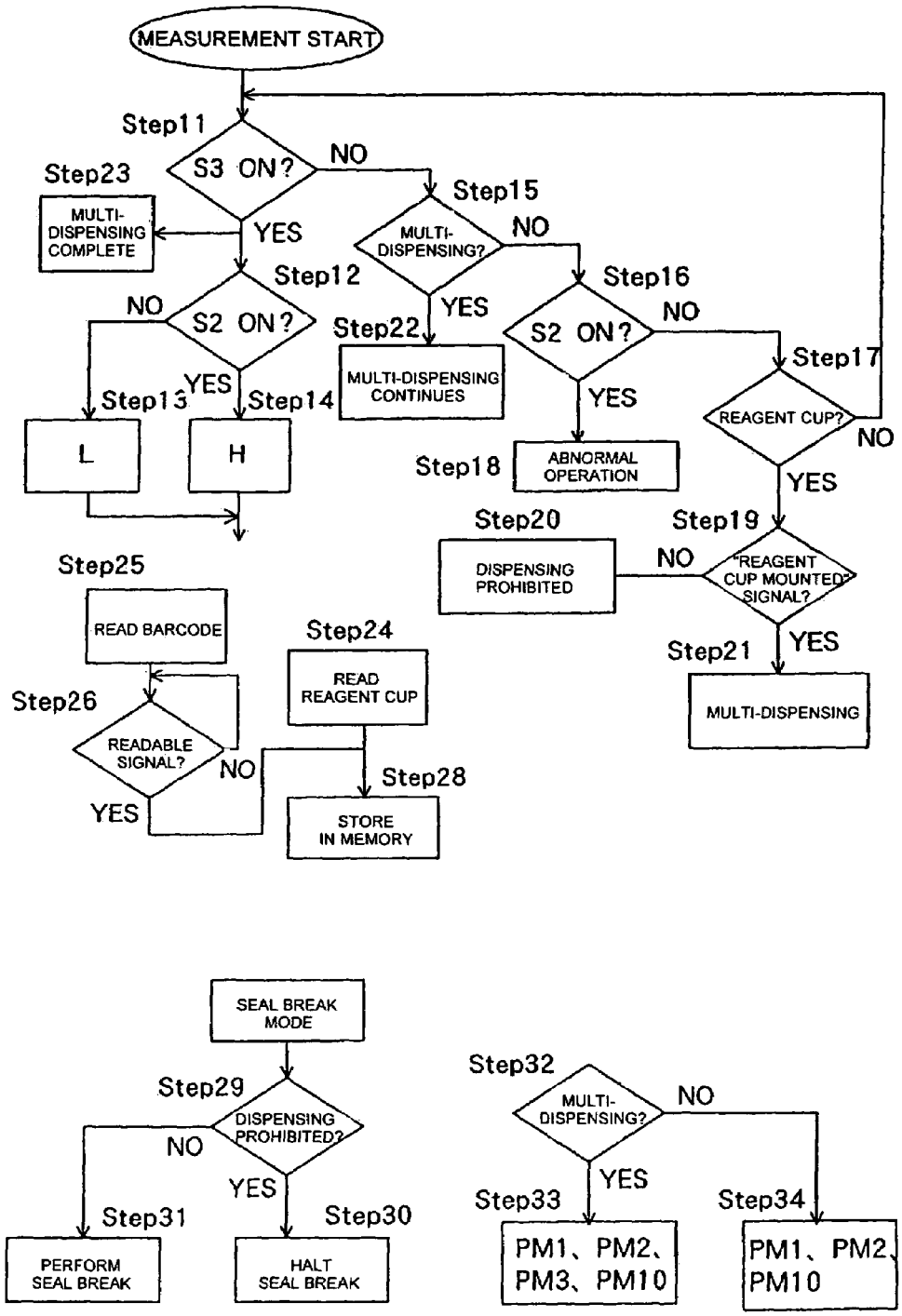
FIG. 9 is a flowchart showing a measurement process for the control device of FIG. 7.

Next is a description of the measurement process, based on the flowchart of FIG. 9.

The measurement process comprises a specimen container height detection mode, a barcode reading mode for reading the barcode on a specimen container, a reagent cup reading mode using a camera 46, a seal break mode using the seal breaker 17, a sample dispensing mode, a BF separation mode, a substrate dispensing mode, and a data analysis mode, and the respective modes are executed independently in parallel. The BF separation mode, the substrate dispensing mode, and the data analysis mode have already been described, and are relatively simple processes, and as such they are omitted from FIG. 9. Furthermore, during the measurement process, the operation described above for washing the BF probe and ejecting air bubbles trapped in the substrate may be conducted every time the carousel 2 reaches the HP, or after several revolutions of the carousel 2.

Once the apparatus has reached a state in which the measurement process can be conducted, the carousel 2 undergoes a 1-step rotation, and a check is made as to whether or not the height detection sensor S3 is ON (Step 11). If the sensor S3 is ON, then the sensor S2 is checked (Step 12), and if the sensor S2 is OFF, then the specimen container is judged to be a short sample cup 9b and a specimen container Low level signal is output (Step 13). If the sensor S2 is ON, then the specimen container is judged to be a tall blood collection tube 9a and a specimen container High level signal is output (Step 14).

If the sensor S3 is OFF at Step 11, then a determination is made as to whether or not the current sample dispensing process is a multi-dispensing (Step 15).

If the result at Step 15 rules out a multi-dispensing, then a check is made as to whether or not the sensor S2 is ON (Step 16), and if the sensor S2 is OFF, a determination is made as to whether or not a reagent cup 6 is mounted in the corresponding cup holder 5 using imaging information from the camera 46 (Step 17).

In the reagent cup reading mode conducted at Step 24, based on the imaging information from the reagent cup 6 captured by the camera 46, (1) if the identification marking is read correctly, a "reagent cup mounted" signal is output, (2) if the presence of a reagent cup 6 can be confirmed but the identification marking on the sealing member 6a is unable to be read, then the sealing member 6a has already been broken and opened, and so an assumption is made that the retrieval of an already measured reagent cup has been overlooked, and a "retrieval forgotten" signal is output, and (3) if the presence of a mounted reagent cup 6 cannot be confirmed, then a "no reagent cup mounted" signal is output. These signals, together with any acquired identification marking information, are stored in memory (Step 28).

If neither of the height detection sensors S2, S3 detect the presence of a specimen container, and no reagent cup is mounted, then the process returns to Step 11, and this subroutine is repeated until the sensor S3 turns ON. Furthermore, if the sensor S2 is ON at Step 16, then a malfunction is judged to have occurred, and an abnormal operation warning is output (Step 18).

At Step 17, if either of the aforementioned "reagent cup mounted" or "retrieval forgotten" signal has been output, then a reagent cup 6 is judged to be present, and the process proceeds to Step 19.

At Step 19, if the "reagent cup mounted" signal has been output, then the process proceeds to Step 21, a multi-dispensing is confirmed, and the sample dispenser 18 conducts injection operations in accordance with a multi-dispensing process. If the "retrieval forgotten" has been output then the process proceeds to Step 20 and injection is prohibited.

Furthermore at Step 15, if the current sample dispensing process is a multi-dispensing, then the multi-dispensing process is continued at Step 22.

The sample dispensing process is conducted under multi-dispensing, and if the maximum of 5 dispensing processes have then been conducted, or if the sensor S3 detects a specimen container at Step 11, then the multi-dispensing ends (Step 23). This completes the specimen container height detection mode.

In the barcode reading mode conducted at Step 25, if the signal is a signal representing the barcode reading result (or a readable signal) (Step 26), it is stored in memory (Step 28).

In the seal break mode using the seal breaker 17, a judgment is made at Step 29 as to whether or not the reagent cup 6 that has arrived at the position B where seal breaking is conducted has been designated "dispensing prohibited". If the cup has been designated "dispensing prohibited" then seal breaking is not performed (Step 30), but otherwise the seal breaking operation is executed (Step 31).

In the sample dispensing mode, a judgment is made at Step 32 as to whether or not a multi-dispensing is in progress, and in the case of a multi-dispensing, the lift motor PM1, the horizontal movement motor PM2, the revolving motor PM3, and the dispensing syringe motor PM10 of the sample dispenser 18 are all activated appropriately. Then, the appropriate number of 1-step rotations from the position C are performed by sequentially increasing the angle of revolution of the revolving motor PM3 to suck a sample from the specimen container, and this sample is then dispensed into the reagent cup 6 at the position C (Step 33). If the dispensing process is not a multi-dispensing, then the lift motor PM1, the horizontal movement motor PM2, and the dispensing syringe motor PM10 are all activated appropriately at Step 34, and the sample dispensing nozzle is moved horizontally and up and down solely at the position C, and a sample from the specimen container is dispensed into the reagent cup 6. Subsequently, before the next dispensing process is started, and regardless of whether or not a multi-dispensing is in progress, the motor PM3 is used to rotate the sample dispensing nozzle 18d to the position D, the motor PM2 is then activated and used to position the sample dispensing nozzle 18d over the dispensing water tank 28, and the motor PM1 is then activated and used to immerse the sample dispensing nozzle 18d in the washing solution inside the dispensing water tank 28, thereby washing the sample dispensing nozzle 18d.

This completes the description of the operation of this embodiment. In this embodiment, pulse motors were used as the drive sources for driving the various members of the immunoassay apparatus, but the present invention is not restricted to this configuration, and any of a variety of other motors can also be used.

Furthermore, the temperature controlling element is not restricted to element for raising the temperature, and where required may also include element for cooling or lowering the temperature, such as heat radiating element formed from a heat conductive metal plate with a series of surface irregularities on the rear surface.

Furthermore in the present embodiment, the stirrer based on the movable magnet plate 8 was used for stirring the reagent and specimen mixtures, but if stirring is unnecessary then the stirrer and associated means may be omitted.

As described above, according to the present invention, a single rotor is used to move specimen containers and reagent-carrying reaction containers in a single direction while dispensing specimen samples into the reaction containers, and the measurements are completed within a single complete rotation, and as a result the overall size of the apparatus can be reduced. Furthermore, because mounting and retrieval of the specimen containers and reagent-carrying reaction containers is conducted at a single location, the operability of the apparatus is good.

According to a fourth aspect of the present invention, because the specimen containers can be mounted at the outer periphery of the rotor, the operations for mounting and retrieving the specimen containers are simple, and furthermore because the reaction containers can be mounted at the upper surface of the rotor, the operations for mounting and retrieving the reaction containers are also simple. Furthermore, because the reagent-carrying reaction containers can be mounted directly opposing the corresponding specimen containers, there is little danger of mounting containers in the wrong position.

According to the fifth aspect of the present invention, reagent-carrying reaction containers can be mounted and retrieved without tall specimen containers causing an impediment to access.

According to the sixth aspect of the present invention, positional control of the rotor is conducted using a rotational angle that corresponds with the positional pitch of the specimen container holders, and consequently the rotor can be moved accurately to the variety of devices disposed around the periphery of the rotor.

According to the seventh aspect of the present invention, the specimen dispenser can be positioned inside the rotor, which contributes to further miniaturization of the apparatus.

According to the eighth aspect of the present invention, because the temperature controlling element is formed in the shape of a circular plate, it occupies little space, and also contacts the lower surfaces of the reaction container holders of the rotor, enabling the reaction containers to be effectively heated via the reaction container holders.

According to the ninth aspect of the present invention, the reaction containers also contact the surface of the heater directly, enabling even more efficient heating of the reaction containers.

According to the tenth aspect of the present invention, by checking whether or not the rotor driver is stopped at its home position when the rotor has reached its home position, a judgment can be made as to whether or not synchronization of the rotor driver with the rotor has been achieved.

According to the eleventh and twelfth aspects of the present invention, when the rotor reaches the rotor home position, a slight back and forth movement of the rotor enables the nozzle device of the washing apparatus to be washed using the washing port provided on the rotor, and also enables any air bubbles trapped in the substrate to be ejected by discharging substrate from the substrate nozzle.

According to the thirteenth and fourteenth aspects of the present invention, the distance below the liquid surface inside the specimen container to which the specimen dispensing nozzle is lowered is determined in accordance with the height of the specimen container held in the specimen container holder of the rotor, and consequently inadvertent overly-deep insertion of the specimen dispensing nozzle into the specimen container can be prevented.

What is claimed is:

1. An automated analyzer, comprising:
   a rotor configured to rotate about a vertical central axis, and including an inner peripheral portion and an outer peripheral portion;
   a specimen container to contain a specimen;
   a plurality of specimen container holders evenly spaced around the outer peripheral portion of the rotor and configured to hold a specimen container;
   a plurality of reagent cups containing a reagent for reacting with the specimen;
   a plurality of reagent cup holders evenly spaced around the inner peripheral portion of the rotor and configured to hold a reagent cup, each reagent cup holder including a main body section and a flange section that extends radially outwards from a bottom of the main body section, wherein the reagent cup, positioned in the one of the plurality of reagent cup holders, extends through a bottom surface of the plurality of reagent cup holders such that the bottom of the reagent cup directly contacts an upper surface of a temperature controlling element;
   a specimen dispenser configured to remove the specimen from the specimen container and configured to dispense the specimen into the reagent cup, wherein the specimen dispenser includes a revolving device configured to revolve a specimen dispensing nozzle about the central axis of the rotor, a radial movement device configured to move the specimen dispensing nozzle along a radial direction of the rotor, and a lift motor configured to raise and lower the specimen dispensing nozzle;
   the temperature controlling element positioned beneath the plurality of reagent cup holders, and one of the plurality of reagent cup holders holds the reagent cup such that said upper surface of the temperature controlling element contacts the flange section at a bottom of the reagent cup holder leaving a gap between an inner peripheral surface of each reagent cup holder and the corresponding reagent cup to heat the reagent cup;
   a stirrer disposed along a movement route of the reagent cup held by any one of the reagent cup holders and configured to stir a mixed solution of the reagent and the specimen in the reagent cup; and
   a data analyzer disposed along the movement route of the reagent cup and configured to analyze the mixed solution, wherein the outer peripheral portion is lower than the inner peripheral portion of the rotor.

2. The automated analyzer according to claim 1, further comprising:
   a washing apparatus disposed around a periphery of the rotor, and configured to wash an inside of the reagent cup with a washing solution and configured to remove the washing solution from the inside of the reagent cup at a position along a rotational direction of the rotor used during measurement where a reaction between the specimen and the reagent has finished.

3. The automated analyzer according to claim 2, further comprising:

a substrate dispenser disposed around the periphery of the rotor at a more downstream position in the rotational direction of the rotor than the washing apparatus, and configured to dispense a substrate into the reagent cup washed by the washing apparatus.

4. The automated analyzer according to claim 1, wherein,
the rotor comprises a rotor main body formed as a cylindrical member, and
the reagent cup holders are provided at a predetermined spacing around a periphery of an upper flange formed on an inner periphery of a top edge of the rotor main body, and
the specimen container holders are provided around an outer periphery of the rotor main body, directly opposing the reagent cup holders.

5. The automated analyzer according to claim 4, wherein when the specimen container is taller than the reagent cup, a top edge of the specimen container held in any one of the specimen container holders and a top edge of the reagent cup held in any one of the reaction reagent cup holders are at substantially a same height.

6. The automated analyzer according to claim 1, wherein the rotor is rotated intermittently, with a single step equivalent to a rotational angle corresponding with a pitch with which the specimen container holders are provided on the rotor.

7. The automated analyzer according to claim 1, wherein the temperature controlling element is formed in a shape of a circular plate.

8. The automated analyzer according to claim 1, further comprising:
a rotor home position detector configured to detect a predetermined stop position of the rotor as a home position of the rotor.

9. The automated analyzer according to claim 3, further comprising:
a rotor home position detector configured to detect a predetermined stop position of the rotor as a home position of the rotor,
wherein the rotor comprises a washing tank into which a nozzle device of the washing apparatus is inserted, which is provided between the washing apparatus and a substrate nozzle of the substrate dispenser when the rotor is positioned at the stop position as the home position of the rotor.

10. The automated analyzer according to claim 9, wherein at the home position of the rotor, the rotor is rotated so that the washing tank moves to, and stops beneath the washing apparatus and beneath the substrate nozzle, and
the washing tank is configured to wash the nozzle device of the washing apparatus and to discharge the substrate from the substrate nozzle to eject any air bubbles trapped in the substrate.

11. The automated analyzer according to claim 1, further comprising:
a specimen container height detector configured to detect a height of the specimen container held in any one of the specimen container holders provided on the rotor.

12. The automated analyzer according to claim 1, further comprising:
a specimen container height detector configured to detect a height of the specimen container held in any one of the specimen container holders provided on the rotor,
wherein a distance below a liquid surface inside the specimen container to which the specimen dispensing nozzle is lowered is determined in accordance with the height of the specimen container detected by the specimen container height detector.

13. The automated analyzer according to claim 1, wherein the temperature controlling element is configured to heat the plurality of reagent cup holders without heating the plurality of specimen container holders.

14. The automated analyzer according to claim 1, wherein each of the plurality of specimen container holders have a larger diameter than each of the plurality of reagent cup holders, and
a center of each of the plurality of specimen container holders and a center of the corresponding reagent cup holder overlap along a radius of the rotor.

* * * * *